United States Patent
Garde et al.

(10) Patent No.: US 10,252,011 B2
(45) Date of Patent: Apr. 9, 2019

(54) SYSTEM AND METHOD FOR INTRA-PULMONARY PERCUSSIVE VENTILATION INTEGRATED WITH A VENTILATOR

(71) Applicant: KONINKLIJKE PHILIPS N.V., Eindhoven (NL)

(72) Inventors: Smita Garde, Irvine, CA (US); Samir Ahmad, San Diego, CA (US); Michael Edward Madison, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 830 days.

(21) Appl. No.: 14/655,778

(22) PCT Filed: Jan. 8, 2014

(86) PCT No.: PCT/IB2014/058122
§ 371 (c)(1),
(2) Date: Jun. 26, 2015

(87) PCT Pub. No.: WO2014/111828
PCT Pub. Date: Jul. 24, 2014

(65) Prior Publication Data
US 2015/0359982 A1    Dec. 17, 2015

Related U.S. Application Data

(60) Provisional application No. 61/753,500, filed on Jan. 17, 2013.

(51) Int. Cl.
*A61M 16/00*    (2006.01)
*A61M 16/06*    (2006.01)
(Continued)

(52) U.S. Cl.
CPC .... *A61M 16/0006* (2014.02); *A61M 16/0051* (2013.01); *A61M 16/0069* (2014.02);
(Continued)

(58) Field of Classification Search
CPC ................ A61M 16/024; A61M 16/06; A61M 16/0875; A61M 16/0051; A61M 16/0069;
(Continued)

(56) References Cited

U.S. PATENT DOCUMENTS

| | | | |
|---|---|---|---|
| 2008/0295839 A1* | 12/2008 | Habashi | A61M 16/0051 128/204.22 |
| 2009/0126731 A1 | 5/2009 | Dunsmore et al. | |
| 2010/0078024 A1* | 4/2010 | Andrieux | A61M 16/0051 128/204.21 |

OTHER PUBLICATIONS

Dellamonica et al: "Intrapulmonary Percussive Ventilation Superimposed on Conventional Ventilation:Bench Study of Humidity and Ventilator Behaviour"; Intensive Care Med (2008) 34:2035-2043.

* cited by examiner

*Primary Examiner* — Gregory A Anderson
*Assistant Examiner* — Margaret M Luarca (57) ABSTRACT

The present disclosure pertains to a ventilation therapy system configured to control a pressure or flow generator to apply an intra-pulmonary percussive ventilation therapy regime to a pressurized flow of breathable gas during baseline ventilation therapy. The ventilation therapy system is configured to automatically control the pressurized flow of breathable gas. The system may automatically control an extent of hyperinflation during IPPV in a subject. The system is configured such that therapy set points, alarm settings, and/or other factors are automatically adjusted during the application of IPPV relative to the set points and alarm settings during baseline ventilation therapy. In some embodiments, the system comprises one or more of a (Continued)

pressure or flow generator, a subject interface, one or more sensors, one or more processors, a user interface, electronic storage, and/or other components.

12 Claims, 7 Drawing Sheets

(51) Int. Cl.
*A61M 16/08* (2006.01)
*A61B 5/087* (2006.01)
*A61B 5/091* (2006.01)
*A61M 16/16* (2006.01)
*A61M 16/20* (2006.01)

(52) U.S. Cl.
CPC .......... *A61M 16/024* (2017.08); *A61M 16/06* (2013.01); *A61M 16/0875* (2013.01); *A61B 5/087* (2013.01); *A61B 5/091* (2013.01); *A61M 16/0063* (2014.02); *A61M 16/0072* (2013.01); *A61M 16/0075* (2013.01); *A61M 16/0096* (2013.01); *A61M 16/161* (2014.02); *A61M 16/201* (2014.02); *A61M 16/204* (2014.02); *A61M 2016/003* (2013.01); *A61M 2016/0024* (2013.01); *A61M 2016/0027* (2013.01); *A61M 2016/0033* (2013.01); *A61M 2205/18* (2013.01); *A61M 2205/332* (2013.01); *A61M 2205/3317* (2013.01); *A61M 2205/3334* (2013.01); *A61M 2205/3365* (2013.01); *A61M 2205/3368* (2013.01); *A61M 2205/3584* (2013.01); *A61M 2205/505* (2013.01); *A61M 2205/52* (2013.01)

(58) Field of Classification Search
CPC .............. A61M 16/003; A61M 16/161; A61M 16/201; A61M 16/0063; A61M 16/0096; A61M 16/0075; A61M 16/0072; A61M 16/204
See application file for complete search history.

SYSTEM AND METHOD FOR INTRA-PULMONARY PERCUSSIVE VENTILATION INTEGRATED WITH A VENTILATOR

CROSS-REFERENCE TO PRIOR APPLICATIONS

This application is the U.S. National Phase application under 35 U.S.C. § 371 of International Application No. PCT/IB2014/058122, filed on Jan. 8, 2014, which claims the benefit of U.S. Provisional Patent Application No. 61/753,500, filed on Jan. 17, 2013. These applications are hereby incorporated by reference herein.

BACKGROUND

1. Field

The present disclosure pertains to a pressure control ventilation or volume control ventilation or pressure support system configured to control a pressure or flow generator to apply an intra-pulmonary percussive ventilation therapy regime to a pressurized flow of breathable gas during baseline ventilation therapy of pressure control ventilation, volume control ventilation, pressure support ventilation or pressure regulated volume control ventilation.

2. Description of the Related Art

Intra-pulmonary percussive ventilation (IPPV) has been used to support secretion mobilization in patients. IPPV typically delivers lower amplitude bursts of gas (~60 lpm) at a high frequency (2 to 6 Hz) to the lungs along with a therapeutic inspiratory and expiratory flow of gas at a typical breath rate. This results in internal percussion of the lungs that opens the airways and improves mucus clearance. One of the devices used for this purpose is the Percussionator. The Percussionator is a standalone device external to a ventilator and is used in conjunction with normal operation of the ventilator. When this device, and/or other similar devices are used to ventilate a patient, IPPV delivery leads to hyperinflation (e.g., high mean airway pressure). A user accordingly manually adjusts settings for tidal volume, pressure control, inspiratory pressure alarm limits, and other alarm limits. Such IPPV delivery is connected to the patient circuit externally and the ventilator does not control the IPPV delivery. This provides additional tidal volume delivered to the patient in addition to the tidal volume delivered by the ventilator and leads to hyperinflation.

SUMMARY

Accordingly, one or more aspects of the present disclosure relate to a pressure control ventilation or volume control ventilation system configured to deliver a pressurized flow of breathable gas to the airway of a subject. The pressure support system comprises a pressure or flow generator, one or more sensors, and one or more processors. The pressure or flow generator is configured to generate a pressurized flow of breathable gas for delivery to the airway of the subject. The one or more sensors are configured to generate output signals conveying information related to one or more gas parameters of the pressurized flow of breathable gas. The one or more processors are configured to execute computer program modules. The computer program modules comprise a therapy module, a percussive pulse module, and an alarm module. The therapy module is configured to control the pressure or flow generator to generate the pressurized flow of breathable gas according to a positive pressure support baseline therapy regime based on the output signals. The percussive pulse module is configured to control the pressure or flow generator to apply an intra-pulmonary percussive ventilation therapy regime to the pressurized flow of breathable gas during the positive pressure support baseline therapy. The alarm module is configured to obtain hyperinflation limit alarm levels for the one or more gas parameters and detect alarm events based on the obtained hyperinflation limit alarm levels. The one or more hyperinflation limit alarm levels include a first hyperinflation limit alarm level for the positive pressure support baseline therapy regime and a second hyperinflation limit alarm level for the intra-pulmonary percussive ventilation therapy regime applied to the positive pressure support baseline therapy regime. The alarm module is configured to detect alarm events based on the first hyperinflation limit alarm level during a first period of time in which the intra-pulmonary percussive ventilation therapy regime is not applied. The alarm module is configured to detect alarm events based on the second hyperinflation limit alarm level during a second period of time in which the intra-pulmonary percussive ventilation therapy regime is applied.

Yet another aspect of the present disclosure relates to a method for delivering a pressurized flow of breathable gas to the airway of a subject with a pressure support system. The pressure support system comprises a pressure or flow generator, one or more sensors, and one or more processors. The one or more processors are configured to execute computer program modules. The computer program modules comprise a therapy module, a percussive pulse module, and an alarm module. The method comprises generating a pressurized flow of breathable gas for delivery to the airway of the subject with the pressure or flow generator; generating output signals conveying information related to one or more gas parameters of the pressurized flow of breathable gas with the one or more sensors; controlling the pressure or flow generator to generate the pressurized flow of breathable gas according to a positive pressure support baseline therapy regime with the therapy module based on the output signals; controlling the pressure or flow generator with the percussive pulse module to apply an intra-pulmonary percussive ventilation therapy regime to the pressurized flow of breathable gas during the positive pressure support baseline therapy; obtaining, with the alarm module, hyperinflation limit alarm levels for the one or more gas parameters; and detecting, with the alarm module, alarm events based on the obtained hyperinflation limit alarm levels, the one or more hyperinflation limit alarm levels including a first hyperinflation limit alarm level for the positive pressure support baseline therapy regime and a second hyperinflation limit alarm level for the intra-pulmonary percussive ventilation therapy regime applied to the positive pressure support baseline therapy regime, wherein, alarm events are detected based on the first hyperinflation limit alarm level during a first period of time in which the intra-pulmonary percussive ventilation therapy regime is not applied, and wherein, alarm events are detected based on the second hyperinflation limit alarm level during a second period of time in which the intra-pulmonary percussive ventilation therapy regime is applied.

Still another aspect of present disclosure relates to a pressure support system configured to deliver a pressurized flow of breathable gas to the airway of a subject. The pressure support system comprising means for generating a pressurized flow of breathable gas for delivery to the airway of a subject; means for generating output signals conveying information related to one or more gas parameters of the pressurized flow of breathable gas; means for controlling the means for generating a pressurized flow to generate the pressurized flow of breathable gas according to a positive pressure support baseline therapy regime based on the output signals; means for controlling the means for generating a pressurized flow to apply an intra-pulmonary percussive ventilation therapy regime to the pressurized flow of breathable gas during the positive pressure support baseline therapy; and means for obtaining hyperinflation limit alarm levels for the one or more gas parameters and detecting alarm events based on the obtained hyperinflation limit alarm levels. The one or more hyperinflation limit alarm levels include a first hyperinflation limit alarm level for the positive pressure support baseline therapy regime and a second hyperinflation limit alarm level for the intra-pulmonary percussive ventilation therapy regime applied to the positive pressure support baseline therapy regime. The means for obtaining is further configured to detect alarm events based on the first hyperinflation limit alarm level during a first period of time in which the intra-pulmonary percussive ventilation therapy regime is not applied. The means for obtaining is further configured to detect alarm events based on the second hyperinflation limit alarm level during a second period of time in which the intra-pulmonary percussive ventilation therapy regime is applied.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
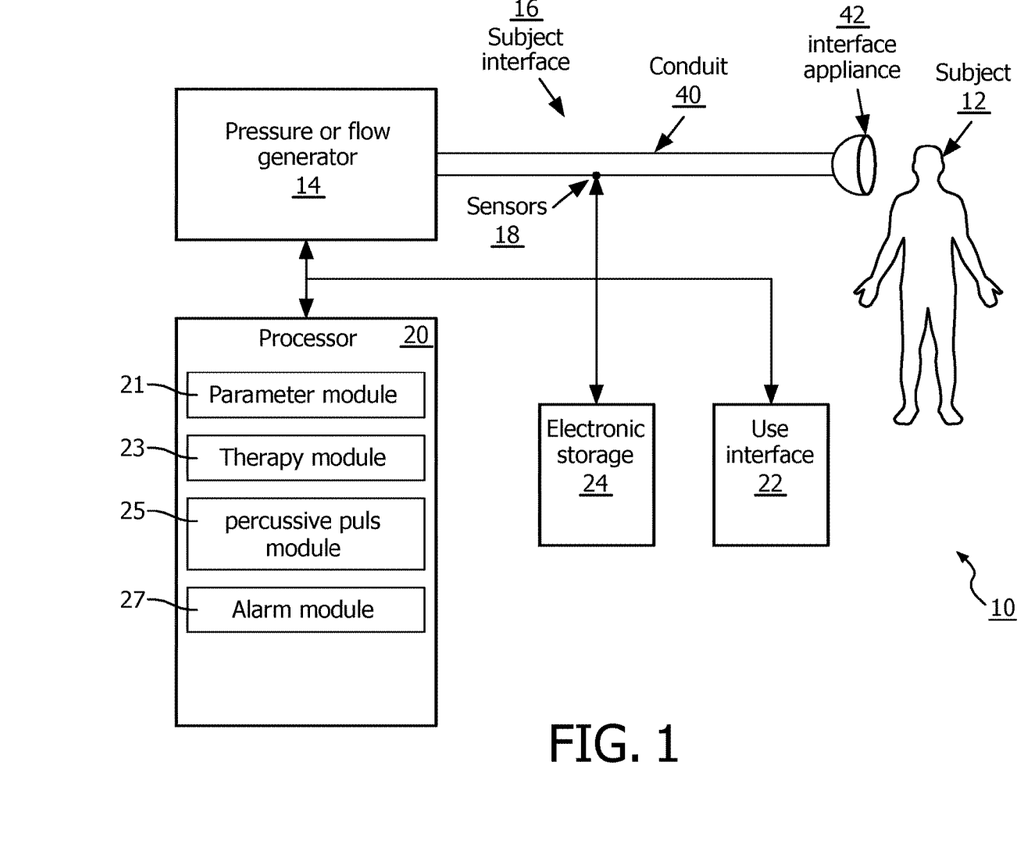
FIG. 1 is a schematic illustration of a pressure support system configured to control a pressure or flow generator to apply an intra-pulmonary percussive ventilation therapy regime to a pressurized flow of breathable gas during positive pressure support baseline therapy.

FIG. 1 schematically illustrates a ventilation therapy system 10 configured to control a pressure or flow generator 14 to apply an intra-pulmonary percussive ventilation (IPPV) therapy regime to a pressurized flow of breathable gas during positive pressure support baseline therapy. The intra-pulmonary percussive therapy is delivered to a subject 12. Ventilation therapy system 10 is configured to provide the pressure support therapy in the form of a pressurized flow of breathable gas that is delivered to the airway of subject 12. Ventilation therapy system 10 is configured to automatically control the pressurized flow of breathable gas. System 10 may automatically control an extent of hyperinflation during IPPV in subject 12. System 10 is configured such that therapy set points (e.g., inspiratory pressure, tidal volume), alarm settings, and/or other factors are automatically adjusted during the application of IPPV relative to the set points and alarm settings during positive pressure support baseline therapy. In some embodiments, system 10 comprises one or more of a pressure or flow generator 14, a subject interface 16, one or more sensors 18, one or more processors 20, a user interface 22, electronic storage 24, and/or other components.

Pressure or flow generator 14 is configured to generate a flow of gas for delivery to the airway of subject 12. Pressure or flow generator 14 may control one or more parameters of the flow of gas (e.g., flow rate, pressure, volume, temperature, gas composition, etc.) for therapeutic purposes, and/or for other purposes. By way of a non-limiting example, pressure or flow generator 14 may be configured to control a pressure level of the flow of gas to apply intra-pulmonary percussive ventilation therapy to the airway of subject 12. The percussive ventilation therapy may be applied to a pressurized flow of breathable gas during positive pressure support baseline therapy.

Pressure or flow generator 14 receives a flow of gas from a gas source, such as the ambient atmosphere, and elevates the pressure of that gas for delivery to the airway of a patient. In some embodiments, pressure or flow generator 14 receives a flow of gas from a gas source through an inlet port. Pressure or flow generator 14 is any device, such as, for example, a pump, blower, compressed gas air or oxygen tank, piston, or bellows, that is capable of elevating the pressure of the received gas for delivery to a patient. Pressure or flow generator 14 may comprise one or more valves for controlling the pressure/flow of gas. The present disclosure also contemplates controlling the operating speed of the blower, either alone or in combination with such valves, to control the pressure/flow of gas provided to the patient.

The one or more valves may be configured to selectively control flow between pressure or flow generator 14 and subject interface 16. In some embodiments, the one or more valves may comprise one or more valves in series and/or in parallel. Examples of valves and/or other pressure regulating devices suitable for use as the one or more valves comprise, a plug valve, a ball valve, a check valve, a butterfly valve, a solenoid, voice-coil actuated valve and/or other pressure regulating devices The pressure regulating devices mentioned above and/or other pressure regulating devices that may be used as the one or more valves may be controlled magnetically, hydraulically, pneumatically, via an electric motor and/or another mode of control configured to open and/or close a valve and/or other pressure control device.

Subject interface 16 is configured to deliver the pressurized flow of breathable gas to the airway of subject 12. As such, subject interface 16 comprises conduit 40, interface appliance 42, and/or other components. Conduit 40 is configured to convey the pressurized flow of gas to interface appliance 42. Conduit 40 may be a flexible length of hose, or other conduit, that places interface appliance 42 in fluid communication with pressure or flow generator 14. Interface appliance 42 is configured to deliver the flow of gas to the airway of subject 12. In some embodiments, interface appliance 42 is non-invasive. As such, interface appliance 42 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 42. Some examples of non-invasive interface appliance 42 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

One or more sensors 18 are configured to generate output signals conveying information related to one or more parameters of the gas within system 10. The one or more parameters of the gas within system 10 may comprise gas parameters related to the pressurized flow of breathable gas, breathing parameters related to respiration of subject 12, and/or other parameters. Sensors 18 may comprise one or more sensors that measure such parameters directly (e.g., through fluid communication with the flow of gas in conduit 40 and/or interface appliance 42). Sensors 18 may comprise one or more sensors that generate output signals related to the one or more parameters indirectly. For example, sensors 18 may comprise one or more sensors configured to generate an output based on an operating parameter of pressure or flow generator 14 (e.g., patient flow and/or pressure estimations from motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters.

Although sensors 18 are illustrated in FIG. 1 at a single location within system 10, this is not intended to be limiting. Sensors 18 may comprise sensors disposed in a plurality of locations, such as for example, at various locations within (or in communication with) conduit 40, within pressure or flow generator 14, within (or in communication with) interface appliance 42, and/or other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., pressure or flow generator 14), or processor 20 may represent processing functionality of a plurality of devices operating in coordination.

As shown in FIG. 1, processor 20 is configured to execute one or more computer program modules. The one or more computer program modules may comprise one or more of a parameter module 21, a therapy module 23, a percussive pulse module 25, an alarm module 27, and/or other modules. Processor 20 may be configured to execute modules 21, 23, 25, and/or 27 by software; hardware; firmware; some combination of software, hardware, and/or firmware; and/or other mechanisms for configuring processing capabilities on processor 20.

It should be appreciated that although modules 21, 23, 25, and 27 are illustrated in FIG. 1 as being co-located within a single processing unit, in embodiments in which processor 20 comprises multiple processing units, one or more of modules 21, 23, 25, and/or 27 may be located remotely from the other modules. The description of the functionality provided by the different modules 21, 23, 25, and/or 27 described below is for illustrative purposes, and is not intended to be limiting, as any of modules 21, 23, 25, and/or 27 may provide more or less functionality than is described. For example, one or more of modules 21, 23, 25, and/or 27 may be eliminated, and some or all of its functionality may be provided by other modules 21, 23, 25, and/or 27. As another example, processor 20 may be configured to execute one or more additional modules that may perform some or all of the functionality attributed below to one of modules 21, 23, 25, and/or 27.

Parameter module 21 is configured to determine one or more parameters within system 10. The one or more parameters within system 10 may comprise gas parameters related to the pressurized flow of breathable gas, breathing parameters related to the respiration of subject 12, and/or other parameters. Parameter module 21 is configured to determine the one or more parameters based on the output signals of sensors 18. The information determined by parameter module 21 may be used for controlling pressure or flow generator 14, stored in electronic storage 24, and/or used for other uses.

The one or more parameters determined by parameter module 21 may include, for example, one or more of a flow rate, a volume, a pressure, humidity, temperature, acceleration, velocity, a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other parameters.

Therapy module 23 is configured to control pressure or flow generator 14 to generate the pressurized flow of breathable gas according to a positive pressure support baseline therapy regime. In some embodiments, therapy module 23 is configured to control pressure or flow generator 14 to generate the pressurized flow of breathable gas according to a baseline ventilation therapy regime. In some embodiments, initial therapy set points may be configurable to a user (e.g., subject 12, a doctor, a caregiver) via user interface 22 and/or other methods. Therapy module 23 is configured to control pressure or flow generator 14 based on information related to the output signals from sensors 18, information determined by parameter module 21, information entered by a user to user interface 22, information determined by therapy module 23 based on previous respiration of subject 12, and/or based on other information.

In some embodiments, the positive pressure support baseline therapy regime dictates an inspiratory pressure level and an expiratory pressure level. In positive airway pressure support therapy the pressurized flow of gas generated by the pressure or flow generator is controlled to replace and/or complement a patient's regular breathing By way of non-limiting example, therapy module 23 may control pressure or flow generator 14 such that the pressure control ventilation provided to the subject via the flow of gas comprises of an inspiratory pressure level and a positive end expiratory pressure (PEEP) level.

In some embodiments, therapy module 23 may be configured to control pressure or flow generator 14 to generate the pressurized flow of breathable gas according to other ventilation modes. The other ventilation modes may include pressure control ventilation (PCV), volume controlled ventilation (VCV), pressure regulated volume control (PRVC), pressure support ventilation (PS), continuous positive airway pressure (CPAP), and/or other ventilation modes. In some embodiments, system 10 may be configured such that therapy module 23 controls pressure or flow generator 14 to change the ventilation mode during the application of the intra-pulmonary percussive ventilation therapy regime.

Percussive pulse module 25 is configured to control pressure or flow generator 14 to apply an intra-pulmonary percussive ventilation therapy regime to the pressurized flow of breathable gas during the baseline ventilation therapy. Percussive pulse module 25 is configured to automatically control pressure or flow generator 14 such that hyperinflation in subject 12 is limited. For example, when pressure or flow generator 14 is operating in a pressure control ventilation mode, percussive pulse module 25 may control an inspiratory flow rate and/or an inspiratory pressure (e.g., by controlling a blower speed and/or one or more valves that are part of pressure or flow generator 14). Percussive pulse module 25 is configured to control pressure or flow generator 14 to apply the intra-pulmonary percussive ventilation therapy regime during one or more of at least a portion of an inhalation of subject 12, or at least a portion of an exhalation of subject 12. In some embodiments, percussive pulse module 25 is configured to control pressure or flow generator 14 to apply the intra-pulmonary percussive ventilation therapy regime continuously during a therapy session. Percussive pulse module 25 is configured to control pressure or flow generator 14 based on the output signals from sensors 18, information determined by parameter module 21, information entered by a user to user interface 22, information determined by percussive pulse module 25 based on previous respiration of subject 12, information determined by alarm module 27, and/or based on other information.

In some embodiments, initial intra-pulmonary percussive ventilation therapy regime parameters may be configurable to a user (e.g., subject 12, a doctor, a caregiver) via user interface 22 and/or other methods. During therapy, percussive pulse module 25 is configured to automatically determine one or more pulse parameters of pulses of the intra-pulmonary percussive ventilation therapy based on information related to the output signals from sensors 18, information determined by parameter module 21, information entered by a user to user interface 22, information determined by percussive pulse module 25 based on previous respiration of subject 12, and/or based on other information. In some embodiments, the pulses comprise individual boluses of breathable gas. In some embodiments, the pulse parameters include one or more of a start timing, and end timing, a duration, a duty cycle, a maximum pressure or flowan amplitude, or a frequency.

Figure 2A:
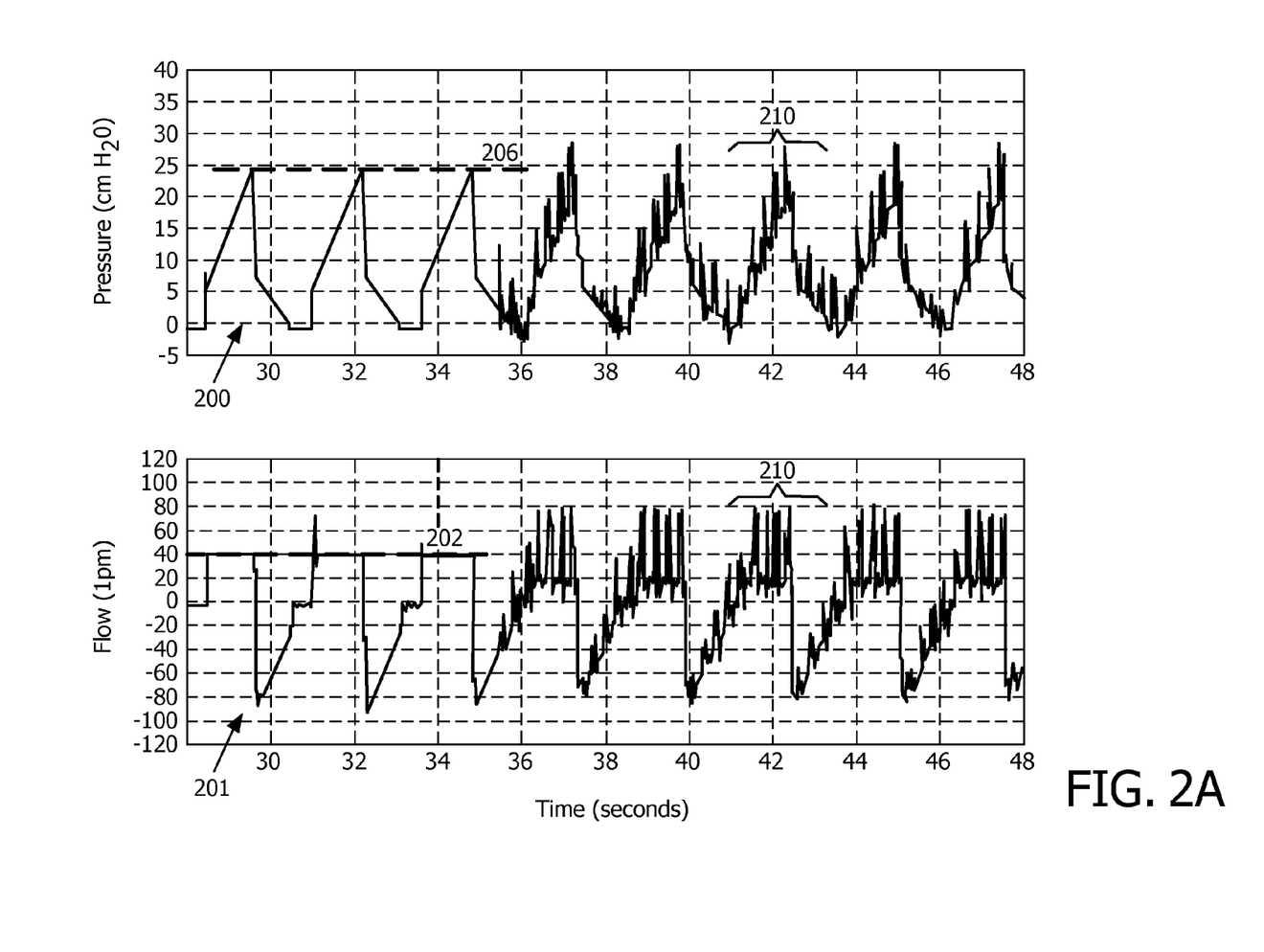
FIG. 2 illustrates intra-pulmonary percussive ventilation therapy delivery with flow rate/volume control ventilation.
Figure 2B:
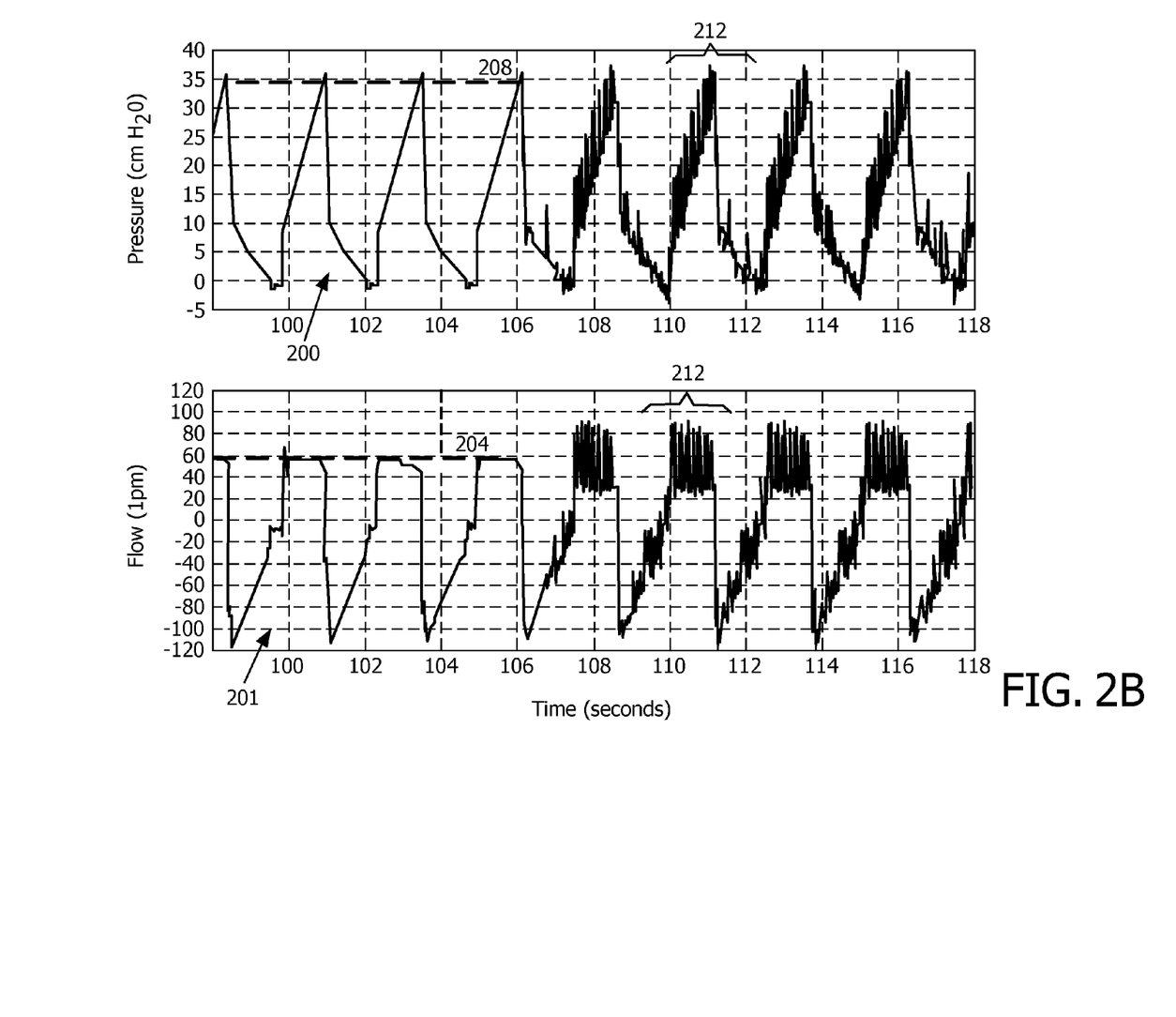

By way of a non-limiting example, FIG. 2 illustrates intra-pulmonary percussive ventilation therapy delivery applied to volume control ventilation (VCV). A therapy module (e.g., therapy module 23 shown in FIG. 1) and/or a percussive pulse module (e.g., percussive pulse module 25 shown in FIG. 1) may control a pressure or flow generator (e.g., pressure or flow generator 14 shown in FIG. 1) to generate pressure/flow rate waves 200, 201. FIG. 2A and FIG. 2B illustrate different peak flow rates 202, 204 and pressures 206, 208 at different IPPV frequencies 210, 212.

Figure 3:
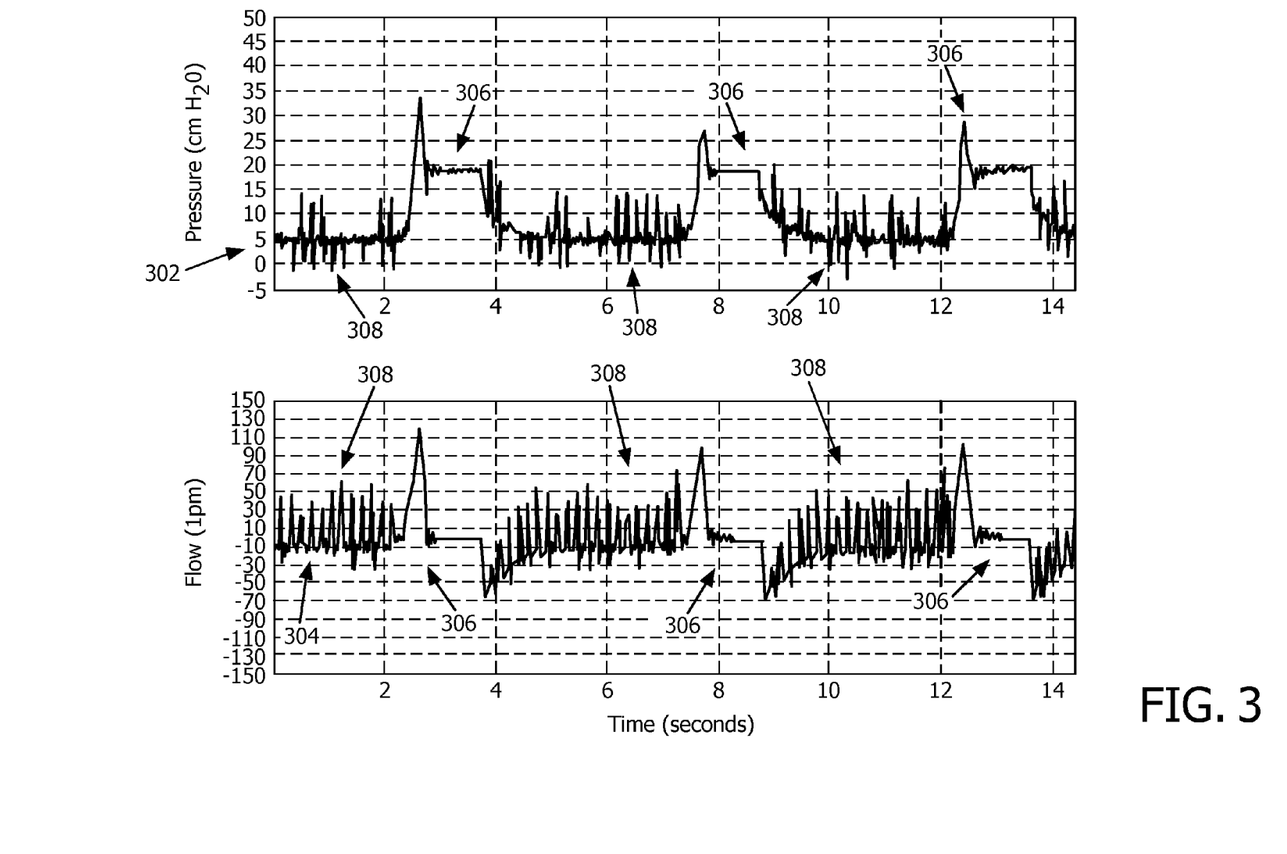
FIG. 3 illustrates intra-pulmonary percussive ventilation therapy applied to pressure control ventilation.

By way of a second non-limiting example, FIG. 3 illustrates intra-pulmonary percussive ventilation therapy delivery applied to pressure control ventilation. Pressure 302 and flow rate 304 waves are shown. In FIG. 3, the intra-pulmonary percussive ventilation therapy is delivered only during exhalation phase 308 (inhalation 306 is also labeled in FIG. 3).

Figure 4A:
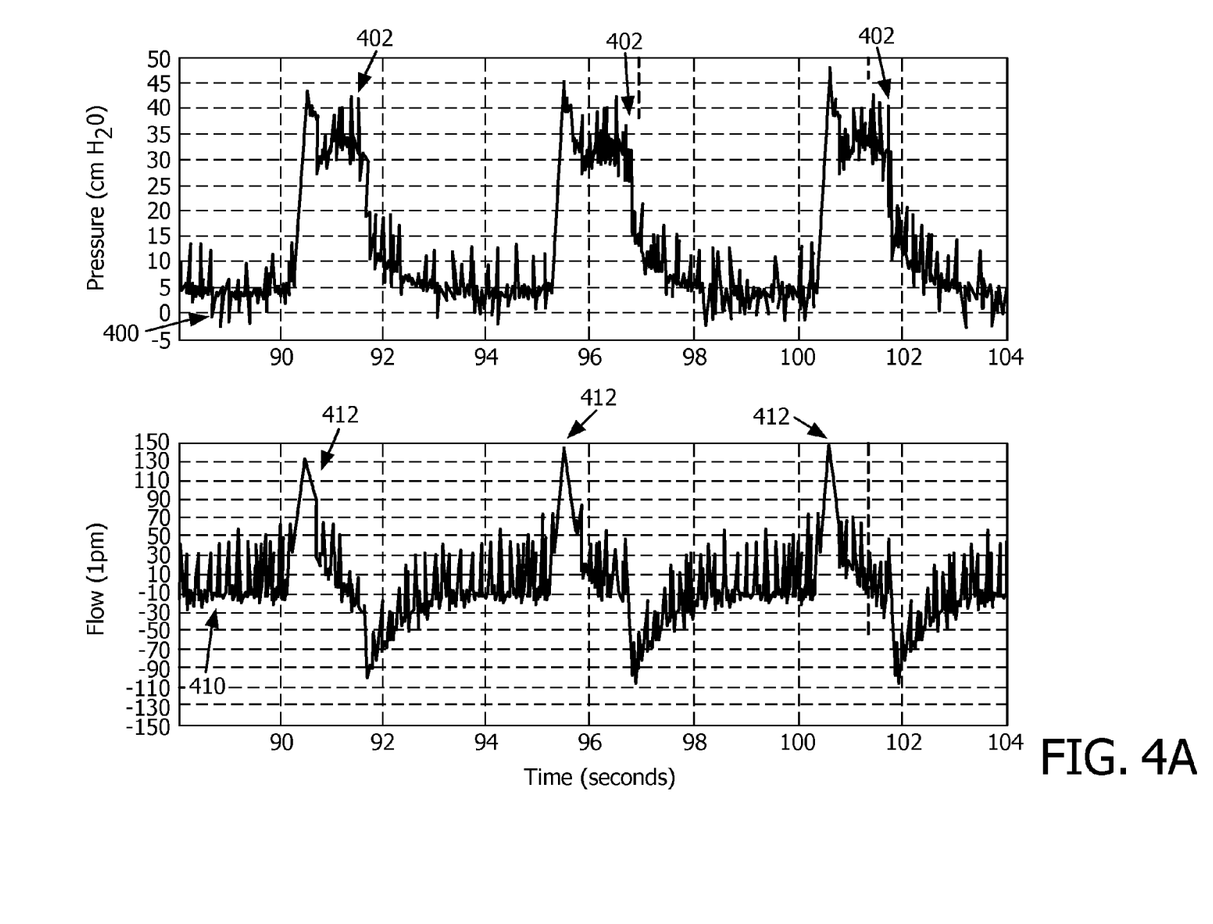
FIG. 4 is a second illustration of intra-pulmonary percussive ventilation therapy applied to pressure control ventilation.
Figure 4B:
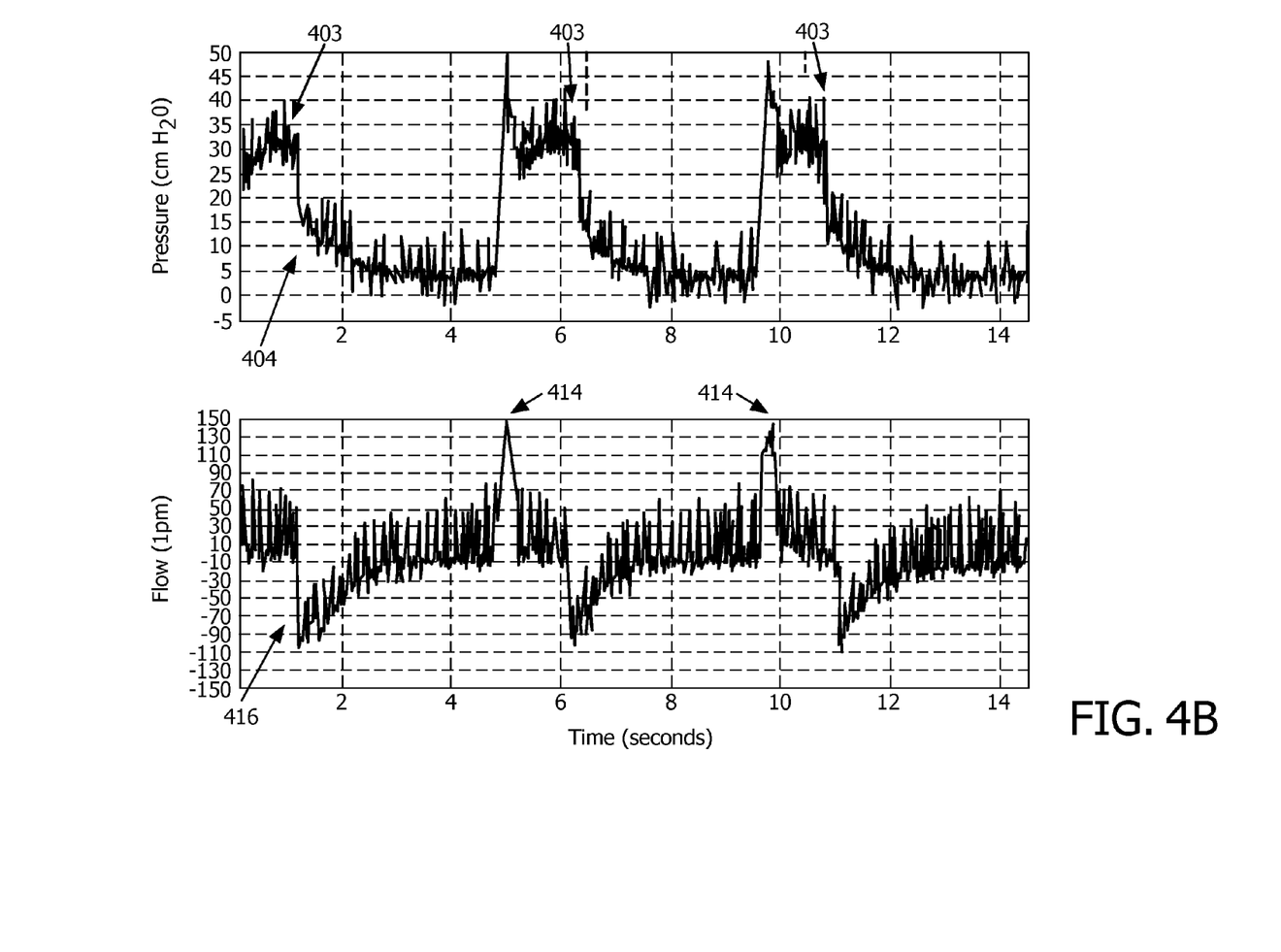

By way of a third non-limiting example, FIG. 4 illustrates intra-pulmonary percussive ventilation therapy delivery applied to pressure control ventilation. FIG. 4A illustrates IPPV therapy applied to pressure control ventilation that is automatically controlled by a therapy module (e.g., therapy module 23 shown in FIG. 1) and/or a percussive pulse module (e.g., percussive pulse module 25 shown in FIG. 1). FIG. 4B illustrates IPPV therapy applied to pressure control ventilation without automatic control. In FIG. 4A, pressure wave 400 has more consistent pressure level 402 during inhalation phase and/or other features compared to pressure levels 403 in pressure wave 404 in FIG. 4B.

Returning to FIG. 1, in some embodiments, therapy module 23 and/or percussive pulse module 25 may be configured to control pressure or flow generator 14 and/or one or more valves of system 10 substantially simultaneously to generate the pressurized flow of breathable gas such that the intra-pulmonary percussive ventilation therapy regime is applied to baseline ventilation therapy regime. In some embodiments, therapy module 23 and/or percussive pulse module 25 may be configured to control flow generator 14 and/or the one or more valves such that levels of one or more gas parameters meet one or more target levels. In some embodiments, therapy module 23 and/or percussive pulse module 25 may be configured to compare a current parameter level (e.g. pressure) to the target level and control pressure or flow generator 14, the one or more valves, and/or other components of system 10 based on the comparison. The one or more target levels may be determined at manufacture, determined by therapy module 23 and/or percussive pulse module 25 based on information received from a user via user interface 22, determined by therapy module 23 and/or percussive pulse module 25 based on previous respiration of subject 12, and/or be determined by other methods.

Alarm module 27 is configured to obtain hyperinflation limit alarm levels for the one or more gas and/or breathing parameters and detect alarm events based on the obtained hyperinflation limit alarm levels. The hyperinflation limit alarm levels may include one or more of a mean airway pressure level, a median airway pressure level, a tidal volume, and/or levels of other gas and/or breathing parameters. In some embodiments, the one or more hyperinflation limit alarm levels include a first hyperinflation limit alarm level for the positive pressure support baseline therapy regime and a second hyperinflation limit alarm level for the intra-pulmonary percussive ventilation therapy regime applied to the positive pressure support baseline therapy regime. The first hyperinflation limit alarm level and the second hyperinflation limit alarm level may be for the same gas/breathing parameter (e.g., mean airway pressure and/or other parameters). Alarm module 27 is configured to obtain the first and the second hyperinflation limit alarm levels automatically. Alarm module 27 is configured to obtain the limit alarm levels based on the output signals, information received from users via user interface 22, information determined by alarm module 27 based on previous respiration of subject 12, and/or other information. Alarm module 27 is configured such that an extent of hyperinflation in subject 12 during the application of the intra-pulmonary percussive ventilation therapy to the positive pressure support baseline therapy is controlled. In some embodiments, alarm module 27 is configured such that the first and the second hyperinflation limit alarm levels are configurable to a user.

Alarm module 27 is configured to detect alarm events based on the first hyperinflation limit alarm level during a first period of time in which the intra-pulmonary percussive ventilation therapy regime is not applied. In some embodiments, therapy module 23 is configured to automatically control pressure or flow generator 14 such that the one or more gas parameters remain within the one or more first hyperinflation limit alarm levels during the positive pressure support baseline therapy.

Alarm module 27 is configured to detect alarm events based on the second hyperinflation limit alarm level during a second period of time in which the intra-pulmonary percussive ventilation therapy regime is applied. In some embodiments, percussive pulse module 25 is configured to control pressure or flow generator 14 such that the one or more gas parameters remain within the second hyperinflation limit alarm level during the application of the intra-pulmonary percussive ventilation therapy to the positive pressure support baseline therapy.

In some embodiments, alarm module 27 is configured to cause one or more components of system 10 to generate an alarm stimulus responsive to the one or more gas parameters breaching the one or more hyperinflation limit alarm levels. The alarm stimulus may comprise, for example, one or more of modulation of the pressurized flow of breathable gas, sounds (e.g., an alarm noise), light (e.g., a flashing light on pressure or flow generator 14), an indicator displayed on user interface 22, and/or other stimuli.

User interface 22 is configured to provide an interface between system 10 and subject 12, and/or other users through which subject 12 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 12) and one or more of pressure or flow generator 14, processor 20, and/or other components of system 10. For example, therapy pressures, pulse parameters, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure or flow generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Figure 5:
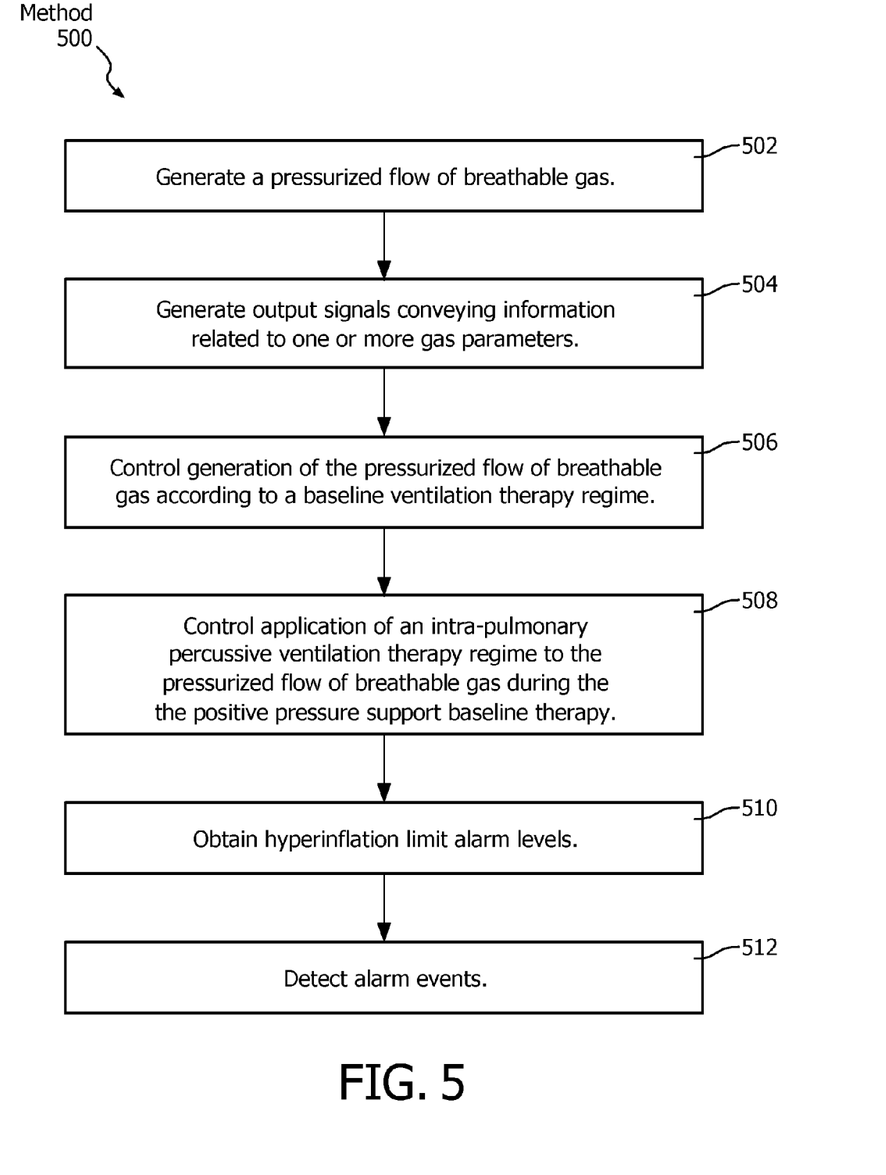
FIG. 5 is a method of controlling a pressure or flow generator to apply an intra-pulmonary percussive ventilation therapy regime to a pressurized flow of breathable gas during positive pressure support baseline therapy.

FIG. 5 illustrates a method 500 for delivering a pressurized flow of breathable gas to the airway of a subject with a pressure support system. The pressure support system comprises a pressure or flow generator, one or more sensors, and one or more processors. The one or more processors are configured to execute computer program modules. The computer program modules comprise a therapy module, a percussive pulse module, and an alarm module. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/ or software to be specifically designed for execution of one or more of the operations of method 500.

At an operation 502, the pressurized flow of breathable gas is generated with the pressure or flow generator. In some embodiments, operation 502 is performed by a pressure or flow generator the same as or similar to pressure or flow generator 14 (shown in FIG. 1 and described herein).

At an operation 504, output signals conveying information related to one or more gas parameters of the pressurized flow of breathable gas are generated with the one or more sensors. In some embodiments, operation 504 is performed by sensors the same as or similar to sensors 18 (shown in FIG. 1 and described herein).

At an operation 506, the pressure or flow generator may be controlled to generate the pressurized flow of breathable gas according to a baseline ventilation therapy regime with the therapy module. The pressure or flow generator may be controlled to generate the pressurized flow of breathable gas according to the baseline ventilation therapy regime based on the output signals. In some embodiments, operation 506 is performed by a computer program module the same as or similar to therapy module 23 (shown in FIG. 1 and described herein.)

At an operation 508, the pressure or flow generator is controlled with the percussive pulse module to apply an intra-pulmonary percussive ventilation therapy regime to the pressurized flow of breathable gas during the baseline ventilation therapy. In some embodiments, operation 508 is performed by a computer program module the same as or similar to percussive pulse module 25 (shown in FIG. 1 and described herein.) At an operation 510, hyperinflation limit alarm levels are obtained with the alarm module for the one or more gas parameters. In some embodiments, operation 510 is performed by a computer program module the same as or similar to alarm module 27 (shown in FIG. 1 and described herein.)

At an operation 512, alarm events are detected with the alarm module. The alarm events are detected based on the obtained hyperinflation limit alarm levels. The one or more hyperinflation limit alarm levels include a first hyperinflation limit alarm level for the positive pressure support baseline therapy regime and a second hyperinflation limit alarm level for the intra-pulmonary percussive ventilation therapy regime applied to the positive pressure support baseline therapy regime. Alarm events are detected based on the first hyperinflation limit alarm level during a first period of time in which the intra-pulmonary percussive ventilation therapy regime is not applied. Alarm events are detected based on the second hyperinflation limit alarm level during a second period of time in which the intra-pulmonary percussive ventilation therapy regime is applied. In some embodiments, operation 512 is performed by a computer program module the same as or similar to alarm module 27 (shown in FIG. 1 and described herein.)

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A ventilation therapy system configured to deliver a pressurized flow of breathable gas to the airway of a subject, the ventilation therapy system comprising:

a pressure or flow generator configured to generate a pressurized flow of breathable gas for delivery to the airway of the subject;

one or more sensors configured to generate output signals conveying information related to one or more gas parameters of the pressurized flow of breathable gas; and one or more processors configured to execute computer program modules, the computer program modules comprising:

a therapy module configured to control the pressure or flow generator to generate the pressurized flow of breathable gas according to a baseline ventilation therapy regime based on the output signals;

a percussive pulse module configured to control the pressure or flow generator to apply an intra-pulmonary percussive ventilation therapy regime to the pressurized flow of breathable gas during baseline ventilation therapy; and an alarm module configured to obtain hyperinflation limit alarm levels for the one or more gas parameters automatically based on the output signals and detect alarm events based on the obtained hyperinflation limit alarm levels, the one or more hyperinflation limit alarm levels including a first hyperinflation limit alarm level for the baseline ventilation therapy regime and second hyperinflation limit alarm level for the intra-pulmonary percussive ventilation therapy regime applied to the baseline ventilation therapy regime, wherein the alarm module is further configured to obtain the first and second hyperinflation limit alarm levels automatically based on the output signals, the output signals being based on a previous respiration of a subject, wherein, the alarm module is further configured to detect alarm events based on the first hyperinflation limit alarm level during a first period of time in which the intra-pulmonary percussive ventilation therapy regime is not applied, and wherein the alarm module is further configured to detect alarm events based on the second hyperinflation limit alarm level during a second period of time in which the intra-pulmonary percussive ventilation therapy regime is applied.

2. The system of claim 1, wherein the percussive pulse module is further configured to control the pressure and flow generator such that a first gas parameter remains within the second hyperinflation limit alarm level during the application of the intra-pulmonary percussive ventilation therapy to baseline ventilation therapy.

3. The system of claim 1, wherein the percussive pulse module is further configured to control the pressure or flow generator to apply the intra-pulmonary percussive ventilation therapy regime during one or more of at least a portion of an inhalation of the subject, or at least a portion of an exhalation of the subject.

4. The system of claim 1, wherein the percussive pulse module is further configured to automatically determine one or more pulse parameters of pulses of the intra-pulmonary percussive ventilation therapy based on the output signals, wherein the pulses comprise individual pulses of breathable gas, and wherein the pulse parameters include one or more of a start timing, an end timing, a duration, a frequency, a pressure level, or a flow level.

5. A method of operating a ventilation therapy system for delivering a pressurized flow of breathable gas to the airway of a subject, the ventilation therapy system comprising a pressure or flow generator, one or more sensors, and one or more processors, the one or more processors configured to execute computer program modules, the computer program modules comprising a therapy module, a percussive pulse module, and an alarm module, the method comprising:

generating a pressurized flow of breathable gas for delivery to the airway of the subject with the pressure or flow generator;

generating output signals conveying information related to one or more gas parameters of the pressurized flow of breathable gas with the one or more sensors;

controlling the pressure or flow generator to generate the pressurized flow of breathable gas according to a baseline ventilation therapy regime with the therapy module based on the output signals;

controlling the pressure or flow generator with the percussive pulse module to apply an intra-pulmonary percussive ventilation therapy regime to the pressurized flow of breathable gas during baseline ventilation therapy;

obtaining, with the alarm module, hyperinflation limit alarm levels for the one or more gas parameters automatically based on the output signals;

detecting, with the alarm module, alarm events based on the obtained hyperinflation limit alarm levels, the one or more hyperinflation limit alarm levels including a first hyperinflation limit alarm level for the baseline ventilation therapy regime and a second hyperinflation limit alarm level for the intra-pulmonary percussive ventilation therapy regime applied to the baseline ventilation therapy regime, obtaining, with the alarm module, the first and second hyperinflation limit alarm levels automatically based on the output signals, the output signals being based on a previous respiration of a subject, such that an extent of hyperinflation in the subject is controlled during the application of the intra-pulmonary percussive ventilation therapy to baseline ventilation therapy; and wherein, alarm events are detected based on the first hyperinflation limit alarm level during a first period of time in which the intra-pulmonary percussive ventilation therapy regime is not applied, and wherein, alarm events are detected based on the second hyperinflation limit alarm level during a second period of time in which the intra-pulmonary percussive ventilation therapy regime is applied.

6. The method of claim 5, further comprising controlling, with the percussive pulse module, the pressure or flow generator such that a first gas parameter remains within the second hyperinflation limit alarm level during the application of the intra-pulmonary percussive ventilation therapy to baseline ventilation therapy.

7. The method of claim 5, further comprising applying, with the percussive pulse module, the intra-pulmonary percussive ventilation therapy regime during one or more of at least a portion of an inhalation of the subject, or at least a portion of an exhalation of the subject.

8. The method of claim 5, further comprising automatically determining, with the percussive pulse module, one or more pulse parameters of pulses of the intra-pulmonary percussive ventilation therapy based on the output signals, wherein the pulses comprise individual boluses of breathable gas, and wherein the pulse parameters include one or more of a start timing, an end timing, a duration, a pressure, or a frequency.

9. A ventilation therapy system configured to deliver a pressurized flow of breathable gas to the airway of a subject, the ventilation therapy system comprising:

means for generating a pressurized flow of breathable gas for delivery to the airway of the subject;

means for generating output signals conveying information related to one or more gas parameters of the pressurized flow of breathable gas; and means for controlling the means for generating a pressurized flow to generate the pressurized flow of breathable gas according to a baseline ventilation therapy regime based on the output signals;

means for controlling the means for generating a pressurized flow to apply an intra-pulmonary percussive ventilation therapy regime to the pressurized flow of breathable gas during baseline ventilation therapy; and means for obtaining hyperinflation alarm limits and alarm module for the one or more gas parameters automatically based on the output signals and detecting alarm events based on the obtained hyperinflation limit alarm levels, the one or more hyperinflation limit alarm levels including a first hyperinflation limit alarm level for the baseline ventilation therapy regime and second hyperinflation limit alarm level for the intra-pulmonary percussive ventilation therapy regime applied to the baseline ventilation therapy regime, wherein the means for obtaining is further configured to obtain the first and second hyperinflation limit alarm levels automatically based on the output signals, the output signals being based on a previous respiration of a subject, wherein, the means for obtaining is further configured to detect alarm events based on the first hyperinflation limit alarm level during a first period of time in which the intra-pulmonary percussive ventilation therapy regime is not applied, and wherein the means for obtaining is further configured to detect alarm events based on the second hyperinflation limit alarm level during a second period of time in which the intra-pulmonary percussive ventilation therapy regime is applied.

10. The system of claim 9, wherein the means for controlling the means for generating a pressurized flow to apply an intra-pulmonary percussive ventilation therapy regime is further configured to control the means for generating a pressurized flow such that a first gas parameter remains within the second hyperinflation limit alarm level during the application of the intra-pulmonary percussive ventilation therapy to baseline ventilation therapy.

11. The system of claim 9, wherein the means for controlling the means for generating a pressurized flow to apply an intra-pulmonary percussive ventilation therapy regime is further configured to apply the intra-pulmonary percussive ventilation therapy regime during one or more of at least a portion of an inhalation of the subject, or at least a portion of an exhalation of the subject.

12. The system of claim 9, wherein the means for controlling the means for generating a pressurized flow to apply an intra-pulmonary percussive ventilation therapy regime is further configured to automatically determine one or more pulse parameters of pulses of the intra-pulmonary percussive ventilation therapy based on the output signals, wherein the pulses comprise individual boluses of breathable gas, and wherein the pulse parameters include one or more of a start timing, an end timing, a duration, a pressure, or a frequency.

* * * * *